(12) United States Patent
Sallares Rosell et al.

(10) Patent No.: US 11,059,851 B2
(45) Date of Patent: Jul. 13, 2021

(54) PROCESS FOR THE PURIFICATION OF METHYLCOBALAMIN

(71) Applicant: INTERQUIM, S.A., Sant Cugat del Vallès (ES)

(72) Inventors: Juan Sallares Rosell, Sant cugat del Vallès (ES); Francisco Marquillas Olondriz, Sant cugat del Vallès (ES)

(73) Assignee: HEALTHTECH BIO ACTIVES, S.L.U., Barcelona (ES)

( * ) Notice: Subject to any disclaimer, the term of this patent is extended or adjusted under 35 U.S.C. 154(b) by 253 days.

(21) Appl. No.: 16/311,091

(22) PCT Filed: Mar. 30, 2017

(86) PCT No.: PCT/EP2017/057506
§ 371 (c)(1),
(2) Date: Dec. 18, 2018

(87) PCT Pub. No.: WO2018/007035
PCT Pub. Date: Jan. 11, 2018

(65) Prior Publication Data
US 2020/0308217 A1    Oct. 1, 2020

(30) Foreign Application Priority Data

Jul. 8, 2016    (EP) .................... 16178560

(51) Int. Cl.
*C07H 23/00*    (2006.01)
*C07H 1/06*    (2006.01)

(52) U.S. Cl.
CPC .............. *C07H 23/00* (2013.01); *C07H 1/06* (2013.01)

(58) Field of Classification Search
None
See application file for complete search history.

(56) References Cited

U.S. PATENT DOCUMENTS

| 3,798,211 A | 3/1974 | Mervyn | |
|---|---|---|---|
| 3,928,320 A * | 12/1975 | Boige | C07F 9/02 536/26.41 |
| 7,220,855 B2 * | 5/2007 | Hisatake | C07H 23/00 536/26.41 |

FOREIGN PATENT DOCUMENTS

| EP | 1236737 A1 | 9/2002 |
|---|---|---|
| GB | 1419933 A | 12/1975 |
| JP | 45-38059 B1 | 12/1970 |

OTHER PUBLICATIONS

DeSilva, Essentials of Ion Exchange, Presented at the 25th Annual WQA Conference Mar. 17, 1999. (Year: 1999).*
Avery et al., "Selective Removal of Cyanide from Industrial Waste Effluents with Ion-Exchange Resins," Ind. Eng. Chem. Prod. Res. Dev., vol. 14, No. 2, 1975, pp. 102-104.
International Search Report and Written Opinion of the International Searching Authority (Forms PCT/ISA/220, PCT/ISA/210, and PCT/ISA/237) for International Application No. PCT/EP2017/057506, dated May 8, 2017.
Ishiyama et al., "New preparation method of methylcobalamin," Meiji Seika Kenkyu Nenpo, vol. 35, 1996, 7 pages, with English abstract.

* cited by examiner

*Primary Examiner* — Layla D Berry
(74) *Attorney, Agent, or Firm* — Birch, Stewart, Kolasch & Birch, LLP

(57) ABSTRACT

The present invention relates to a process for the purification of methylcobalamin, namely from iron cyanide impurities, comprising contacting a solution comprising methylcobalamin and iron cyanide anions with a strongly basic anion exchange resin. This purification process can advantageously be used for removing iron cyanide impurities from methylcobalamin obtained by reductive methylation of cyanocobalamin and wherein iron (II) salts are used as cyanide scavengers, thus providing methylcobalamin with a reduced iron content. Methylcobalamin (R is methyl).

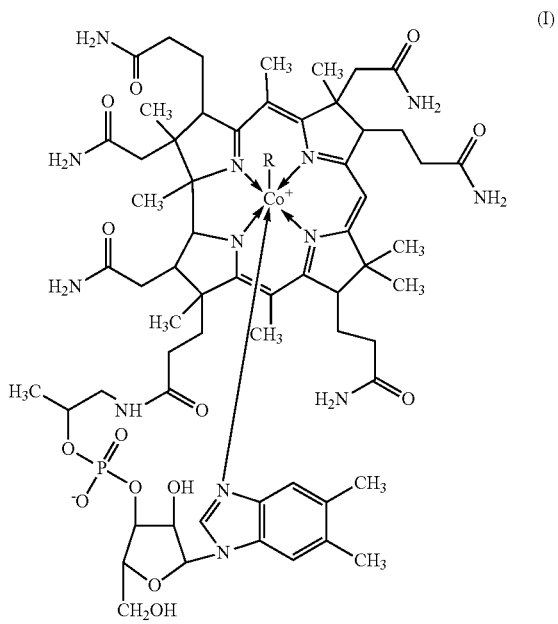

19 Claims, No Drawings

PROCESS FOR THE PURIFICATION OF METHYLCOBALAMIN

This application claims the benefit of European Patent Application EP16178560.5 filed on 8 Jul. 2016.

TECHNICAL FIELD

The present invention relates to a process for the purification of methylcobalamin, which is one of the coenzyme forms of vitamin $B_{12}$.

BACKGROUND ART

Cobalamins are a group of closely related and interconvertible cobalt coordination compounds, which are usually collectively known as vitamin $B_{12}$.

Cobalamins belong to the family of corrinoids, which share a planar tetrapyrrolic ring (corrin ring) containing a central cobalt atom, which may assume an oxidation state of (I), (II) or (III). Additionally, cobalamins possess an upper (beta) and a lower (alpha) axial ligands, as represented in the following structure:

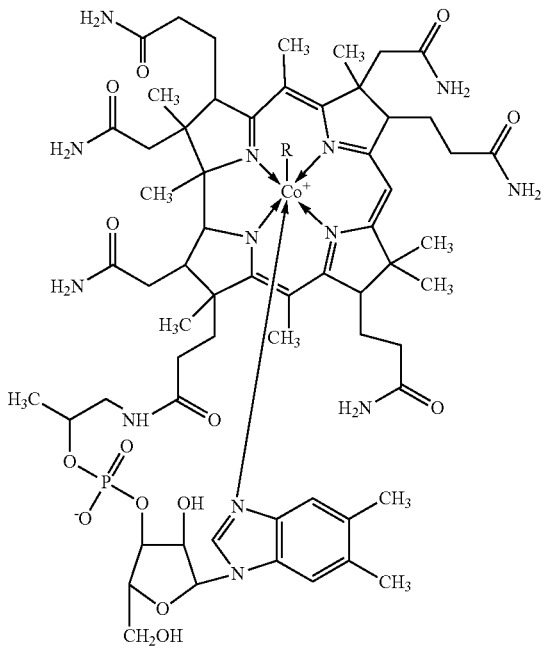

The lower ligand (alpha) is the dimethylbenzimidazole group of a nucleotide, which is connected to the corrin ring through an amide bond. In the naturally occurring cobalamins, the beta ligand (R) may be a cyano-, hydroxo-, methyl- or 5'-deoxyadenosyl-group, giving rise, respectively, to cyanocobalamin, hydroxocobalamin, methylcobalamin, and 5'-deoxyadenosylcobalamin. Usually, the term vitamin $B_{12}$ refers specifically to cyanocobalamin, i.e., when R is the cyano group (CN).

Among the cobalamins, methylcobalamin and 5'-deoxyadenosylcobalamin are the active forms that function as coenzymes for metabolic reactions in the organism, namely in those reactions catalysed by the enzymes methionine synthase and methylmalonyl-CoA mutase, which are related, for example, to red blood cell formation, neurological function, and DNA synthesis. Consequently, vitamin $B_{12}$ deficiency is associated with several pathologies, such as megaloblastic anaemia, fatigue, weakness, constipation, loss of appetite, weight loss, and neurological disorders. In such deficiency states, the administration of cobalamins is indicated.

Methylcobalamin, in particular, is successfully used in therapy for treating several disorders associated to vitamin $B_{12}$ deficiency, for example, for treating peripheral neuropathy or megaloblastic anaemia.

There is, therefore, a need for industrial methods for preparing cobalamins, particularly methylcobalamin, which are both industrially efficient and suitable to provide a high purity product, fulfilling the requirements of the regulatory health organizations.

Methylcobalamin is commonly obtained from cyanocobalamin, by means of a reductive methylation process, involving the treatment of cyanocobalamin with a reducing agent and with a methylating agent. In such process, however, the cyanide anions, which are released from cyanocobalamin during the reduction reaction, tend to bond again to the reduced form of cobalamin, known as cob(I)alamin or vitamin $B_{12S}$, competing with the methylating agent and, thus, lowering the overall reaction yield of the process.

To face this drawback, it has been proposed in the state of the art that this reaction can be advantageously performed in the presence of an agent able to act as cyanide scavenger, i.e., by complexing the cyanide anions present in the reaction media and thus avoiding any interference with the methylation process. Among the suitable cyanide scavengers for this process, several metallic salts have been disclosed, particularly, iron (II) salts.

Thus, in the Japanese patent JP45038059-B1 the preparation of methylcobalamin is disclosed by treatment of cyanocobalamin with sodium borohydride as reducing agent, adding ferrous sulphate heptahydrate as cyanide scavenger, and using methyl iodide as methylating agent. The obtained reaction product is purified by successive phenol extractions and by column chromatography.

Similarly, in the U.S. Pat. No. 3,798,211 several metal salts are proposed as cyanide-complexing agents for the reductive alkylation reaction of cyanocobalamin, particularly copper (II) and iron (II) salts. Thus, the preparation of methylcobalamin from cyanocobalamin is disclosed using ferrous sulphate as cyanide-complexing agent and methyl toluene-p-sulphonate as methylating agent. The product obtained is purified by column chromatography.

In the article Ishiyama et al, New preparation method of methylcobalamin, Meiji Seika Kenkyu Nenpo, 1996, 35: 51-54, the preparation of methylcobalamin from cyanocobalamin is also disclosed, wherein the reaction is carried out in strictly oxygen-free conditions, maintaining the oxygen concentration under 0.1 ppm, and using sodium borohydride and methyl iodide as reducing and methylating agents, respectively, and a mixture of iron (II) and iron (III) salts as cyanide-scavengers, namely, ammonium iron (II) sulphate (Mohr's salt) and iron (III) chloride. The methylcobalamin thus obtained is purified by successive crystallizations, or by column chromatography using a divinylbenzene-styrene copolymer.

The European patent application EP1236737-A1 discloses the preparation of methylcobalamin by reductive methylation of cyanocobalamin using trimethylsulfoxonium or trimethylsulfonium halide salts as methylating agents, and using iron (II) sulphate heptahydrate and/or cobalt (II) chloride hexahydrate as cyanide scavenging agents.

One inconvenient of the above strategy is that the iron salts, which are efficient for improving the performance of the reductive methylation process, may lead to iron residues in the final pharmaceutical substance, and consequently in the final drug product.

Particularly, the removal of iron cyanide anions, formed by complexing of the iron salts with the cyanide anions present in the reaction media, has proved to be challenging, making it difficult to obtain methylcobalamin with an iron content within the limits recommended by the regulatory agencies for metal residues. The European Medicines Agency, for example, recommends maximum acceptable concentration limits of metals arising from the use of metal catalysts or metal reagents in pharmaceutical substances (EMEA/CHMP/SWP/4446/2000).

The processes disclosed hitherto in the art for preparing methylcobalamin require burdensome purification steps, usually including liquid chromatographic separations, which are generally regarded as not well suited for industrial use. Moreover, the documents of the state of the art do not even specifically face the problem of reducing the iron content to acceptable levels.

Therefore, there is a need in the art for an improved purification method which simply and effectively removes iron cyanide anions from mixtures with methylcobalamin, which is suitable for industrial application, so as to enable cost-effective production of methylcobalamin with acceptable levels of iron according to the regulatory agencies.

OBJECT OF THE INVENTION

The object of the present invention is a process for the purification of methylcobalamin.

DETAILED DESCRIPTION OF THE INVENTION

The object of the present invention is a process for the purification of methylcobalamin from mixtures with iron cyanide anions characterized in that it comprises contacting a solution comprising methylcobalamin and iron cyanide anions with a strongly basic anion exchange resin.

The authors of the present invention have developed a new process for the purification of methylcobalamin based on the treatment with a strongly basic anion exchange resin, which, surprisingly, allows the efficient removal of traces of iron cyanide anions present in methylcobalamin solutions using a simple process which can be easily industrially implemented to provide methylcobalamin with a reduced iron content.

This process can advantageously be used for removing iron cyanide impurities from methylcobalamin obtained by reductive methylation of cyanocobalamin wherein iron (II) salts are used as cyanide scavengers, thus providing methylcobalamin with a reduced iron content.

As used in the present description, the singular forms preceded by "a", "an" or "the" are intended to include the plural forms as well, unless the context clearly indicates otherwise. The term approximately as used in the present description indicates that a certain variation of the stated value is admitted, namely of ±10%, preferably of ±5%.
Strongly Basic Anion Exchange Resin An anion exchange resin, as is well known in the art, is an insoluble polymeric matrix containing anions which are able to be exchanged with other anions in solutions which come in contact with them.

A strongly basic anion exchange resin, as the one used in the present invention, is a particular type of anion exchange resin wherein the anion which is exchanged is the counterion of a quaternary ammonium group which is bound to the polymeric matrix of the resin, typically a trialkylammonium group such as trimethylammonium, or a dialkyl 2-hydroxyethyl ammonium group. Preferably, the resin has trialkylammonium functional groups, more preferably trimethylammonium groups.

The counterion, which is exchanged, is generally a chloride or a hydroxide anion. Preferably, the counterion is a chloride anion.

The polymeric matrix of the resin can be a crosslinked polystyrene-divinylbenzene polymer, i.e., prepared from styrene and divinylbenzene as cross-linking agent; or can be a crosslinked acrylic polymer, prepared from acrylic acid, methacrylic acid, or esters of acrylic or methacrylic acid, e.g. methyl, ethyl or propyl esters, crosslinked with e.g. divinylbenzene, ethyleneglycol dimethacrylate, ethyleneglycol divinyl ether, or diethyleneglycol divinyl ether.

In an embodiment of the invention, the resin is selected from a crosslinked polystyrene-divinylbenzene resin and a crosslinked acrylic-divinylbenzene resin. In a preferred embodiment, the resin is a crosslinked acrylic-divinylbenzene resin.

The resins are generally available in form of beads. According to its porosity, the resin can be microporous (gel-type) or macroporous (macroreticular).

Preferably, the resin has macroreticular structure.

In a preferred embodiment, the strongly basic anion exchange resin is a resin having trialkylammonium functional groups and interchanging chloride anions. More preferably, the resin is a crosslinked acrylic-divinylbenzene resin having macroreticular structure.

A number of strongly basic anion exchange resins suitable to be used in the process of the present invention are commercially available, for example, Amberlite® IRA458 RF CI, Amberlite® IRA900 CI, Amberlite® IRA958 CI; Diaion® SA10A(CI), Diaion® HPA25(CI), Dowex® Marathon A, Dowex® Marathon MSA, Lewatit® MonoPlus MP500, Lewatit® MonoPlus MP800, or the strongly basic anion exchange resins from the company Purolite, for example of the Purolite® A200 or Purolite® A500 series; among others.

The commercially available resin Amberlite® IRA958 CI is particularly preferred. It is a macroreticular, strongly basic anion exchange resin having quaternary ammonium functionality in a crosslinked acrylic polymer matrix and interchanging chloride anions.
Purification Process The purification process according to the present invention can advantageously be used for removing iron cyanide impurities from methylcobalamin obtained by reductive methylation of cyanocobalamin wherein iron (II) salts are used as cyanide scavengers.

This purification process is particularly useful for removing residual amounts, namely trace amounts, of iron cyanide anions which still remain as impurities of methylcobalamin, even after having removed a large proportion of the iron cyanide formed in the process by filtering off insoluble iron cyanide salts.

Though not limiting, the amount of residual iron cyanide impurities contained in methylcobalamin, which are to be removed with the process of the current invention by treatment with the resin, is generally equivalent to less than 6000 ppm of iron, preferably less than 5000 ppm of iron, more preferably less than 4000 ppm of iron, and still more preferably less than 1600 ppm.

The process of contacting the solution comprising methylcobalamin and iron cyanide anions with the strongly basic anion exchange resin is preferably performed by passing the solution through an effective amount of the resin.

Typically, a column is filled with an adequate amount of the resin and the solution comprising methylcobalamin and iron cyanide anions is passed through it, either in down-flow or in upper-flow, and the resulting solution is subsequently collected. In a preferred embodiment, the solution is passed in upper-flow.

The solution is passed through the resin over a certain period of time, generally comprised between 2 and 6 hours, and more preferably comprised between 3 and 4 hours.

The strongly basic anion exchange resin is used in a weight ratio resin:methylcobalamin generally comprised between 0.1:1 and 2:1, and more preferably comprised between 0.3:1 and 1:1.

In a particularly preferred embodiment, the weight ratio resin:methylcobalamin is approximately 0.5:1.

Preferably, after having passed the solution through the resin, an amount of solvent alone is subsequently passed through the resin to collect the methylcobalamin that can remain within the resin.

By treatment with a strongly basic anion exchange resin, the iron cyanide anions present in the solution are retained by the resin, while the counterion of the resin, typically the chloride anion, is in turn released.

Within the meaning of the present invention, iron cyanide anions are meant to be anionic iron (II) or iron (III) complexes with cyanide. Typically, among the iron cyanide anions are the ferrocyanide anions, also known as hexacyanoferrate (II) anions ($[Fe(CN)_6]^{4-}$) and the ferricyanide anions, also known as hexacyanoferrate (III) anions ($[Fe(CN)_6]^{3-}$). The iron cyanide anions present as impurities of methylcobalamin may be a mixture of different iron cyanide complexes.

Without wishing to be bound to any particular theory, when methylcobalamin is the result of a reductive methylation process of cyanocobalamin using Fe (II) as cyanide scavenger, the ferrocyanide anion is believed to be a major part of the iron cyanide impurities contained therein.

The anion interchange that takes place between the anion exchange resin and the ferrocyanide anions can be represented as follows:

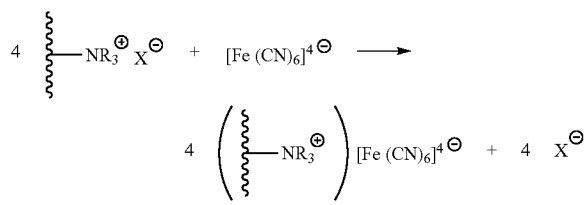

It was surprisingly found that, despite the presence of a large coordination compound as methylcobalamin in the solution, which might itself interact with the iron cyanide anions, the anion interchange between the resin counterion and the iron cyanide anions is effectively performed, and allows obtaining a methylcobalamin solution with a reduced iron content.

As shown in Example 3, the methylcobalamin obtained by reductive methylation of cyanocobalamin using iron salts as cyanide-scavengers could be effectively separated from iron cyanide impurities using the method of the present invention, thus obtaining methylcobalamin having less than 130 ppm of iron, namely 71 ppm or even less than 30 ppm, whereas when the same process was performed without using a strongly basic anion exchange resin, the level of iron in methylcobalamin was much higher, 494 or 1594 ppm.

Upon usage, the anion exchange resin progressively loses its capacity of anion exchanging, as more iron cyanide anions get retained into it. The exhausted resin can be regenerated with an aqueous solution of a salt of the resin counterion, preferably an aqueous solution of a chloride salt, more preferably an aqueous solution of sodium chloride.

The solvent used for performing the purification process, in which methylcobalamin and the iron cyanide anions are dissolved, can be water or a mixture of water with a water-miscible organic co-solvent. Suitable organic co-solvents include, but are not limited to, alcohols such as methanol, ethanol, n-propanol, isopropanol or tert-butanol; ketones such as acetone or 2-butanone; ethers such as 1,4-dioxane, tetrahydrofuran, dimethoxyethane or diglyme; and mixtures thereof.

In a preferred embodiment, the solvent is a mixture of water and a water-miscible organic co-solvent, preferably a mixture of water and a water-miscible co-solvent selected from an alcohol, a ketone and mixtures thereof; more preferably the solvent is a mixture of water and a water-miscible ketone, and still more preferably is a mixture of water and acetone.

The volume proportion water:organic solvent is generally comprised between 1.8:1 and 1:1.5, preferably comprised between 1.5:1 and 1:1.2, more preferably comprised between 1.1:1 and 1:1.1.

In a particularly preferred embodiment, the solvent is a mixture of water and acetone in approximately 1:1 volume proportion.

The solution containing methylcobalamin and the iron cyanide impurities which is contacted with the anion exchange resin comprises methylcobalamin in a concentration generally comprised between 30-150 g/L, preferably between 40-100 g/L, and more preferably comprised between 50-75 g/L.

After performing the treatment with the anion exchange resin, methylcobalamin can be isolated by crystallizing or precipitating it from the solution, generally adding a ketone solvent to the solution, preferably adding acetone to the solution.

In a preferred embodiment of the invention, the solution which is subjected to the purification process is prepared by treating the crude methylcobalamin comprising iron cyanide impurities with the solvent and heating to a temperature comprised between 30° C. and 60° C., preferably between 40° C. and 50° C., and more preferably at approximately 45° C., during a period of time generally comprised between 15 and 60 minutes. The suspension thus obtained is generally filtered to remove the insoluble impurities, for example, insoluble iron cyanide salts, and the filtered solution, still containing residual iron cyanide anions, is then contacted with the strongly basic anion exchange resin, according to the process of the invention.

Therefore, in a particularly preferred embodiment of the invention, the purification of methylcobalamin comprises the following steps:
  treating methylcobalamin, comprising iron cyanide impurities, with the solvent, heating to a temperature comprised between 30° C. and 60° C., and filtering to remove insoluble iron cyanide salts;
  contacting the solution obtained in the previous step, comprising methylcobalamin and iron cyanide anions, with a strongly basic anion exchange resin; and
  isolating methylcobalamin by crystallizing or precipitating it from the solution.

wherein the preferred conditions for each of these steps are as previously disclosed.

The methylcobalamin obtained after performing the process of the invention has a reduced iron content, namely, the amount of iron is less than 130 ppm, preferably less than 90 ppm, still more preferably less than 80 ppm, and still more preferably less than 70 ppm of iron.

The determination of the iron amount can be performed, for example, by inductively coupled plasma optical emission spectrometry (ICP/OES).

Therefore, it is apparent that the method of the invention, involving the use of a strongly basic anion exchange resin, allows the efficient removal of residual iron cyanide anions from methylcobalamin.

Then, another aspect of the present invention is the use of a strongly basic anion exchange resin for removing iron cyanide anions from methylcobalamin.

Methylcobalamin

The methylcobalamin containing iron cyanide impurities, which is susceptible to be purified with the process of the invention, is typically the result of a reductive methylation reaction of cyanocobalamin, performed in the presence of iron (II) salts and optionally iron (III) salts as cyanide scavengers.

The reductive methylation of cyanocobalamin is typically carried out by treatment of cyanocobalamin with a reducing agent and a methylating agent.

The starting product, cyanocobalamin (CAS number 68-19-9) is commercially available from several sources.

The reducing agent can be any agent capable of reducing the cobalt of cyanocobalamins from Co(III) to Co(I). Suitable reducing agents are, for example, alkaline metal borohydrides. A preferred reducing agent is sodium borohydride.

The amount of reducing agent is not particularly limited, but is generally comprised between 5 and 30 equivalents, preferably between 10 and 20 equivalents to cyanocobalamin.

Any suitable methylating agent can be employed, for example, trimethylsulfonium bromide, trimethylsulfonium chloride, trimethylsulfonium methylsulphate, trimethylsulfoxonium chloride, trimethylsulfoxonium iodide, trimethylsulfoxonium bromide, dimethyl carbonate, dimethyl sulphate, tetramethylammonium chloride or methyl iodide. Preferably, the methylating agent is selected from the group consisting of trimethylsulfonium bromide, trimethylsulfonium chloride, trimethylsulfoxonium chloride, trimethylsulfoxonium iodide, trimethylsulfoxonium bromide and dimethyl carbonate.

The amount of methylating agent employed is generally comprised between 1 and 10 equivalents, preferably between 2 and 5 equivalents to cyanocobalamin.

The reductive methylation reaction is performed in aqueous media, optionally in combination with a water-miscible organic co-solvent. Suitable co-solvents are, for example, alcohols such as methanol, ethanol, n-propanol, isopropanol or tert-butanol; ketones such as acetone or 2-butanone; ethers such as 1,4-dioxane, tetrahydrofuran, dimethoxyethane or diglyme; amides such as dimethylformamide, or dimethylacetamide; and mixtures thereof. As co-solvents, preferably alcohols or ketones are used.

The reaction is preferably carried out at slightly basic pH, e.g. 7.5-8.5, and at a temperature in the range 5-60° C., preferably in the range 20-40° C.

An iron (II) salt is added to the reaction as cyanide scavenger, for example, iron (II) sulphate, iron (II) chloride, or ammonium iron (II) sulphate (Mohr's salt). The cyanide ions released in the reduction reaction are complexed by the iron (II) cation to form anionic iron (II) cyanide complexes, for example, the ferrocyanide complex $[Fe(CN)_6]^{4-}$, thus avoiding that they interfere with the methylation process.

The iron (II) salt is employed in an amount generally comprised between 0.5 and 1.5 equivalents to cyanocobalamin, and preferably approximately 1 equivalent of iron (II) salt to cyanocobalamin is employed.

Preferably, an iron (III) salt is also added, typically to form insoluble salts with the ferrocyanide anion, thus allowing their simple removal by filtration.

The reaction is generally performed by dissolving cyanocobalamin, an iron (II) salt, and optionally an iron (III) salt, and adding, sequentially or simultaneously, the reducing agent and the methylating agent.

Cyanocobalamin and methylcobalamin solutions are known to be susceptible photo-oxidation, therefore, the reductive methylation process is preferably performed under inert atmosphere, for example under flow of an inert gas such as nitrogen, and in absence of light, under red-light illumination.

After the reductive methylation reaction, methylcobalamin is generally precipitated from the reaction mixture, by cooling the reaction media, typically also adding further organic solvent, and filtering the crude methylcobalamin.

The crude methylcobalamin thus obtained, contains salts containing iron cyanide anions, and can be then purified using the process of the present invention, so it is made into a solution, by treating it with a suitable solvent, as disclosed above.

The following examples are provided by way of illustration and should not be construed as limiting the present invention.

EXAMPLES

Example 1: Purification Process According to the Invention a) Reductive Methylation of Cyanocobalamin To a stirred mixture of 20 Kg of cyanocobalamin, 0.68 Kg of iron (II) sulphate heptahydrate and 1.77 Kg of 30% aqueous solution of iron (III) chloride in 10 L of methyl ethyl ketone and 260 L of deionized water, at 30-40° C., in inert atmosphere and red light, were added simultaneously over a period of 3 h a solution of 8 Kg of sodium borohydride and 0.16 Kg of aqueous solution of sodium hydroxide in 40 L of deionized water, and 14 L of methyl ethyl ketone. After stirring 30 min at the same temperature, a solution of 7.5 kg of trimethylsulfoxonium bromide in 40 L of deionized water was added over a period of 1 h. After stirring for 3 h at the same temperature, the mixture was cooled to 10° C. and 15 L of methyl ethyl ketone were added, the mixture was stirred for 12 h at the same temperature. The precipitated product was filtered and washed with 100 L of methyl ethyl ketone and 100 L of acetone.

b) Purification of Methylcobalamin

The crude methylcobalamin obtained according to process a) was treated with 300 L of 50% acetone aqueous solution, warmed at 45° C. for 30 min and filtered. The solution was then passed through 10 Kg of Amberlite® IRA 958 Cl resin in backflow system over a period of 4 h. Then, the column was backwashed with 100 L of 50% acetone aqueous solution. The collected solution was adjusted to pH 6.5 with diluted hydrochloric acid. Then was added dropwise 950 L of acetone and stirred for 12 h. The product crystallized was filtered and dried to give 18.0 Kg (yield 83.5%, HPLC=87.9%).

The content of iron impurity in the methylcobalamin was less than 30 ppm, determined by inductively coupled plasma/optical emission spectrometry (ICP/OES). (Batch A)

A second batch (batch B) and third batch (batch C) of methylcobalamin were prepared according to the same processes a) and b) disclosed above. Methylcobalamin was obtained in a yield of 84.4% and 87.9%, respectively, and the iron content was 71 ppm and less than 30 ppm, respectively.

Example 2: Comparative Example

To a stirred mixture of 20 Kg of cyanocobalamin, 0.68 Kg of iron (II) sulphate heptahydrate and 1.77 Kg of 30% aqueous solution of iron (III) chloride in 10 L of methyl ethyl ketone and 260 L of deionized water, at 30-40° C., in inert atmosphere and red light, were added simultaneously over a period of 3 h a solution of 8 Kg of sodium borohydride and 0.16 Kg of aqueous solution of sodium hydroxide in 40 L of deionized water, and 14 L of methyl ethyl ketone. After stirring 30 min at the same temperature, a solution of 7.5 kg of trimethylsulfoxonium bromide in 40 L of deionized water was added over a period of 1 h. After stirring for 3 h at the same temperature, the mixture was cooled to 10° C. and 15 L of methyl ethyl ketone were added, the mixture was stirred for 12 h at the same temperature. The precipitated product was filtered and washed with 100 L of methyl ethyl ketone and 100 L of acetone. The solid was treated with 260 L of 50% acetone aqueous solution, warmed at 45° C. for 30 min and filtered. The solution was cooled to 20° C. and the pH adjusted at 6.5 with diluted hydrochloric acid. 950 L of acetone were added dropwise and stirred for 12 h. The product crystallized was filtered and dried to give 17.8 Kg (yield 84.3%, HPLC=98.9%).

The content of iron impurity in the methylcobalamin was 494 ppm, determined by inductively coupled plasma/optical emission spectrometry (ICP/OES).
(Batch 1)

A second batch (batch 2) of methylcobalamin was prepared according to the same process disclosed above. Methylcobalamin was obtained in a yield of 86.7%, and the iron content was 1594 ppm.

Example 3: Iron Content Comparison

The following table shows the comparison of iron content of methylcobalamin obtained using the method of the present invention for purifying the methylcobalamin obtained after reductive methylation in presence of iron (II) (Example 1, batches A, B and C), and the iron content of methylcobalamin prepared by an analogous method, but without the purification method of the present invention (Comparative example, batches 1 and 2):

| Example | Yield (%) | Fe (ppm) |
| --- | --- | --- |
| Example 1 (batch A) | 83.5 | <30 |
| Example 1 (batch B) | 84.4 | 71 |
| Example 1 (batch C) | 87.9 | <30 |
| Comparative example (batch 1) | 84.3 | 494 |
| Comparative example (batch 2) | 86.7 | 1594 |

The invention claimed is:

1. Process for the purification of methylcobalamin from mixtures with iron cyanide anions characterized in that it comprises contacting a solution comprising methylcobalamin and iron cyanide anions with a strongly basic anion exchange resin.

2. Process according to claim 1, characterized in that the strongly basic anion exchange resin has trialkylammonium functional groups and interchanges chloride anions.

3. Process according to claim 1, characterized in that the resin is selected from a crosslinked polystyrene-divinylbenzene resin and a crosslinked acrylic-divinylbenzene resin.

4. Process according to claim 1, characterized in that the resin is a crosslinked acrylic-divinylbenzene resin having macroreticular structure.

5. Process according to claim 1, characterized in that the process of contacting the solution comprising methylcobalamin and iron cyanide anions with the strongly basic anion exchange resin is performed by passing the solution through an effective amount of the resin over a period of time comprised between 2 and 6 hours.

6. Process according to claim 1, characterized in that the weight ratio resin:methylcobalamin is comprised between 0.1:1 and 2:1.

7. Process according to claim 6, characterized in that the weight ratio resin:methylcobalamin is approximately 0.5:1.

8. Process according to claim 1, characterized in that the solvent used in the solution is selected from water and a mixture of water with an water-miscible organic co-solvent.

9. Process according to claim 8, characterized in that the solvent is a mixture of water and a water-miscible organic co-solvent.

10. Process according to claim 9, characterized in that the solvent is a mixture of water and acetone.

11. Process according to claim 9, characterized in that the volume proportion water:organic co-solvent is comprised between 1.8:1 and 1:1.5.

12. Process according to claim 1, characterized in that methylcobalamin is crystallized from the solution collected after the treatment with the resin.

13. Process according to claim 1, characterized in that the solution which is subjected to the purification process is prepared by treating methylcobalamin comprising iron cyanide impurities with the solvent, heating to a temperature comprised between 30° C. and 60° C., and filtering to remove insoluble impurities.

14. Process according to claim 1, characterized in that the methylcobalamin which is purified is obtained by reductive methylation of cyanocobalamin in the presence of iron (II) salts and optionally iron (III) salts as cyanide scavengers.

15. Process according to claim 1, characterized in that the methylcobalamin obtained has a content of iron of less than 130 ppm.

16. Process according to claim 2, characterized in that the resin is selected from a crosslinked polystyrene-divinylbenzene resin and a crosslinked acrylic-divinylbenzene resin.

17. Process according to claim 2, characterized in that the resin is a crosslinked acrylic-divinylbenzene resin having macroreticular structure.

18. Process according to claim 3, characterized in that the resin is a crosslinked acrylic-divinylbenzene resin having macroreticular structure.

19. Process according to claim 2, characterized in that the process of contacting the solution comprising methylcobalamin and iron cyanide anions with the strongly basic anion exchange resin is performed by passing the solution through an effective amount of the resin over a period of time comprised between 2 and 6 hours.

* * * * *